United States Patent
Nakagawa et al.

(10) Patent No.: US 10,398,409 B2
(45) Date of Patent: Sep. 3, 2019

(54) TRANSDUCER COVER, METHOD FOR FORMING THE COVER, AND ULTRASONIC MEDICAL INSTRUMENT WITH THE COVER

(75) Inventors: Masaki Nakagawa, Kanuma (JP); Shinichi Tanaka, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 1 day.

(21) Appl. No.: 12/954,853

(22) Filed: Nov. 27, 2010

(65) Prior Publication Data
US 2011/0130664 A1   Jun. 2, 2011

(30) Foreign Application Priority Data

Nov. 27, 2009   (JP) ................................ 2009-269978

(51) Int. Cl.
| | |
|---|---|
| *A61B 8/00* | (2006.01) |
| *A61N 7/00* | (2006.01) |
| *A61C 1/07* | (2006.01) |
| *A61B 17/32* | (2006.01) |
| *A61C 17/20* | (2006.01) |

(Continued)

(52) U.S. Cl.
CPC ........ *A61B 8/44* (2013.01); *A61B 17/320068* (2013.01); *A61C 1/07* (2013.01); *A61C 17/20* (2013.01); *A61N 7/00* (2013.01); *A61B 8/4444* (2013.01); *A61B 8/4455* (2013.01); *A61B 8/46* (2013.01); *A61B 8/546* (2013.01);
(Continued)

(58) Field of Classification Search
CPC .. A61C 17/20; A61C 1/07; A61C 1/00; A61C 1/08; A61N 7/00; A61N 2007/0004; A61B 8/44; A61B 17/320068; A61B 8/46; A61B 8/546; A61B 8/4444; A61B 8/4455

USPC ........ 601/2–4; 604/20, 22; 438/6, 15, 22, 23, 438/24, 25, 26, 48, 51, 55, 106, 112; 257/787–798, 678, 629, 632, 634, 635, 257/636, 637, 638, 646, 254, 416, 433; 600/459

See application file for complete search history.

(56) References Cited

U.S. PATENT DOCUMENTS 4,936,310 A * 6/1990 Engstrom .......... A61B 5/02154
                                                   600/486
5,130,950 A * 7/1992 Orban et al. .................... 367/34

(Continued)

FOREIGN PATENT DOCUMENTS

| JP | H-04-279070 A | 10/1992 |
|---|---|---|
| JP | 2001-017439 | 1/2001 |

(Continued)

*Primary Examiner* — Amanda Lauritzen Moher
(74) *Attorney, Agent, or Firm* — Jason D. Voight

(57) ABSTRACT

A transducer cover for use in an ultrasonic medical instrument having a transducer is disclosed. The transducer cover includes a vibration absorbing layer of a generally cylindrical form made of a synthetic resin having a vibration absorbing property, and a chemical blocking layer of a generally cylindrical form made of a synthetic resin which is impermeable to water and chemicals. The vibration absorbing layer and the chemical blocking layer are coaxially laminated, and capable of sealing arrangement over and around the transducer. Also disclosed is an ultrasonic medical instrument having an ultrasonic transducer and the transducer cover, and a method for forming the transducer cover over and around an ultrasonic transducer of an ultrasonic medical instrument.

4 Claims, 8 Drawing Sheets

(51) Int. Cl.
  *A61C 1/08* (2006.01)
  *A61C 1/00* (2006.01)
(52) U.S. Cl.
  CPC ............... *A61C 1/00* (2013.01); *A61C 1/08* (2013.01); *A61N 2007/0004* (2013.01)

(56) References Cited

U.S. PATENT DOCUMENTS

| | | | |
|---|---|---|---|
| 5,928,154 A * | 7/1999 | Silber | B25G 1/10 600/459 |
| 6,193,709 B1 * | 2/2001 | Miyawaki et al. | 606/1 |
| 6,322,532 B1 * | 11/2001 | D'Sa et al. | 604/22 |
| 6,613,066 B1 * | 9/2003 | Fukaya | A61M 25/1029 606/192 |
| 6,716,028 B2 | 4/2004 | Rahman et al. | |
| 7,011,520 B2 | 3/2006 | Rahman et al. | |
| 7,548,014 B2 * | 6/2009 | Asada et al. | 310/348 |
| 2005/0095556 A1 | 5/2005 | Pollock et al. | |
| 2005/0256518 A1 * | 11/2005 | Rama | A61B 17/2202 606/27 |
| 2008/0064006 A1 | 3/2008 | Quan et al. | |
| 2008/0077017 A1 * | 3/2008 | Hyuga | A61B 8/12 600/459 |
| 2008/0218030 A1 * | 9/2008 | Asada | G10K 9/22 310/334 |
| 2010/0003636 A1 * | 1/2010 | Wagner | A61C 5/62 433/89 |
| 2011/0004127 A1 * | 1/2011 | Okada et al. | 601/2 |

FOREIGN PATENT DOCUMENTS

| | | | |
|---|---|---|---|
| JP | 2002-113020 A | | 4/2002 |
| JP | 2005-095243 A | | 4/2005 |
| JP | 2007-509714 A | | 4/2007 |
| WO | WO 93/05715 | * | 4/1993 ............ A61B 17/20 |

* cited by examiner

TRANSDUCER COVER, METHOD FOR FORMING THE COVER, AND ULTRASONIC MEDICAL INSTRUMENT WITH THE COVER

FIELD OF ART

The present invention relates to a transducer cover for use in an ultrasonic medical instrument, such as an ultrasonic handpiece, as well as to a method for forming the transducer cover, and an ultrasonic medical instrument with the transducer cover.

BACKGROUND ART

In the medical art, ultrasonic handpieces employing a piezoelectric element (ultrasonic transducer) have hitherto been used for treatment of living tissues, such as cutting or removal of bones or teeth. As an example of such ultrasonic handpieces, JP-2005-95243-A1 discloses an ultrasonic handpiece for dental treatment, which is used for endodontic therapy, such as treatment of pulpal diseases and periapical periodontitis, or removal of tartar. The ultrasonic handpiece disclosed in this publication has an ultrasonic generator in a cylindrical body casing, and a tip attached to the distal end of the body casing and vibrated by the ultrasonic generator.

In general, this type of ultrasonic generator has, as shown in FIG. 7, front horn 71 located in the distal part of the body casing, rear horn 72 connected to the front horn 71 and located in the proximal part of the body casing, and transducer 73 arranged and held between the front and rear horns 71 and 72. In order to fix the ultrasonic generator in the body casing, and to block or reduce transmission of vibration of the transducer 73 to the body casing during treatment, transducer cover 74 is attached over and around the transducer 73. The transducer cover 74 used for this type of handpiece is usually an annular molded rubber product having elasticity, and fits over and around the transducer 73. The ultrasonic generator is placed in the body casing via the transducer cover 74, and a connector is connected to the proximal end of the body casing for supplying power and cooling water to the ultrasonic generator. When powered, the transducer 73 generates ultrasonic mechanical vibration, which is amplified by the front horn 71 and transmitted to the tip to vibrate the tip in the longitudinal direction of the front horn 71.

In clinical practice, tools and devices used in treatment are subjected to various sterilization processes after each treatment in order to prevent infection with various pathogenic bacteria among patients. Ultrasonic handpieces are not an exception and are usually subjected to high pressure steam sterilization such as autoclaving. To this end, the transducer cover used in ultrasonic handpieces is made of silicon rubber or the like material having excellent resistance to water, heat, and chemicals, so as to prevent steam and chemicals from permeating through the transducer cover and adhering to the electrodes of the transducer, which causes insulation deterioration of the transducer.

In order to enhance prevention of infection with various pathogenic bacteria among patients via medical tools and devices, it is recently recommended to subject the tools and devices to washing with hot water containing alkaline chemicals, in addition to the conventional high pressure steam sterilization or other sterilization.

However, when ultrasonic handpieces are washed with hot water containing alkaline chemicals, the chemicals often permeate the transducer cover even if it is made of silicon rubber, and adhere to the electrodes of the transducer to cause insulation degradation of the transducer. As a result, ultrasonic vibration is weakened and the original performance cannot be delivered.

Ultrasonic handpieces are also subjected to washing with hot water containing acidic chemicals, or immersion cleaning in alkaline or acidic chemicals. These procedures also have similar problems as described above.

SUMMARY OF THE INVENTION

It is an object of the present invention to securely block the permeation of chemicals into the transducer cover of an ultrasonic medical instrument which is subjected to washing with hot water containing alkaline or acidic chemicals or immersion cleaning in alkaline or acidic chemicals, and to securely prevent insulation failure of the transducer caused by adhesion of the chemicals to the electrodes of the transducer.

According to the present invention, there is provided a transducer cover for use in an ultrasonic medical instrument having a transducer, comprising:

a vibration absorbing layer of a generally cylindrical form made of a synthetic resin having a vibration absorbing property, and a chemical blocking layer of a generally cylindrical form made of a synthetic resin which is impermeable to water and chemicals, wherein said vibration absorbing layer and said chemical blocking layer are coaxially laminated, and capable of sealing arrangement over and around the transducer.

Of the two coaxial layers, the vibration absorbing layer may be the inner layer, and the chemical blocking layer may be the outer layer.

The chemical blocking layer may extend beyond the vibration absorbing layer at least distally to cover the distal end of the vibration absorbing layer.

The vibration absorbing layer may be made of rubber having a vibration absorbing property. The chemical blocking layer may be made of rubber having resistance to water, heat, and chemicals, and rendered impermeable by compression molding.

According to the present invention, there is also provided an ultrasonic medical instrument comprising:

an ultrasonic transducer for generating vibration, and a transducer cover arranged over and around the ultrasonic transducer, said transducer cover comprising:

a vibration absorbing layer of a generally cylindrical form made of a synthetic resin having a vibration absorbing property, and a chemical blocking layer of a generally cylindrical form made of a synthetic resin which is impermeable to water and chemicals, wherein said vibration absorbing layer and said chemical blocking layer are coaxially laminated and sealingly attached over and around the ultrasonic transducer.

The vibration absorbing layer may be sealingly attached to the ultrasonic transducer as the inner layer, and the chemical blocking layer may be sealingly attached to the vibration absorbing layer as the outer layer.

The chemical blocking layer may extend beyond the vibration absorbing layer at least distally to cover the distal end of the vibration absorbing layer.

The vibration absorbing layer may be made of rubber having a vibration absorbing property. The chemical blocking layer may be made of rubber having resistance to water, heat, and chemicals, and impermeable to water and chemicals.

According to the present invention, there is further provided a method for forming a transducer cover over and around an ultrasonic transducer of an ultrasonic medical instrument, comprising:

arranging a cylindrical member around the ultrasonic transducer, said cylindrical member being made of a synthetic resin impermeable to water and chemicals, arranging an elastic, thermosetting synthetic resin material in liquid form inside or outside of said cylindrical member in contact therewith to form a layer, vacuum defoaming said synthetic resin in liquid form, and thermally curing said synthetic resin in liquid form, whereby a transducer cover having a vibration absorbing layer and a chemical blocking layer is formed sealingly laminated over and around the ultrasonic transducer.

The above step of arranging the synthetic resin material in liquid form may be carried out by introducing the synthetic resin material in liquid form between the cylindrical member and the ultrasonic transducer.

PREFERRED EMBODIMENTS OF THE INVENTION

The present invention will now be explained in detail with reference to the preferred embodiments taken in conjunction with the attached drawings.

Figure 1:
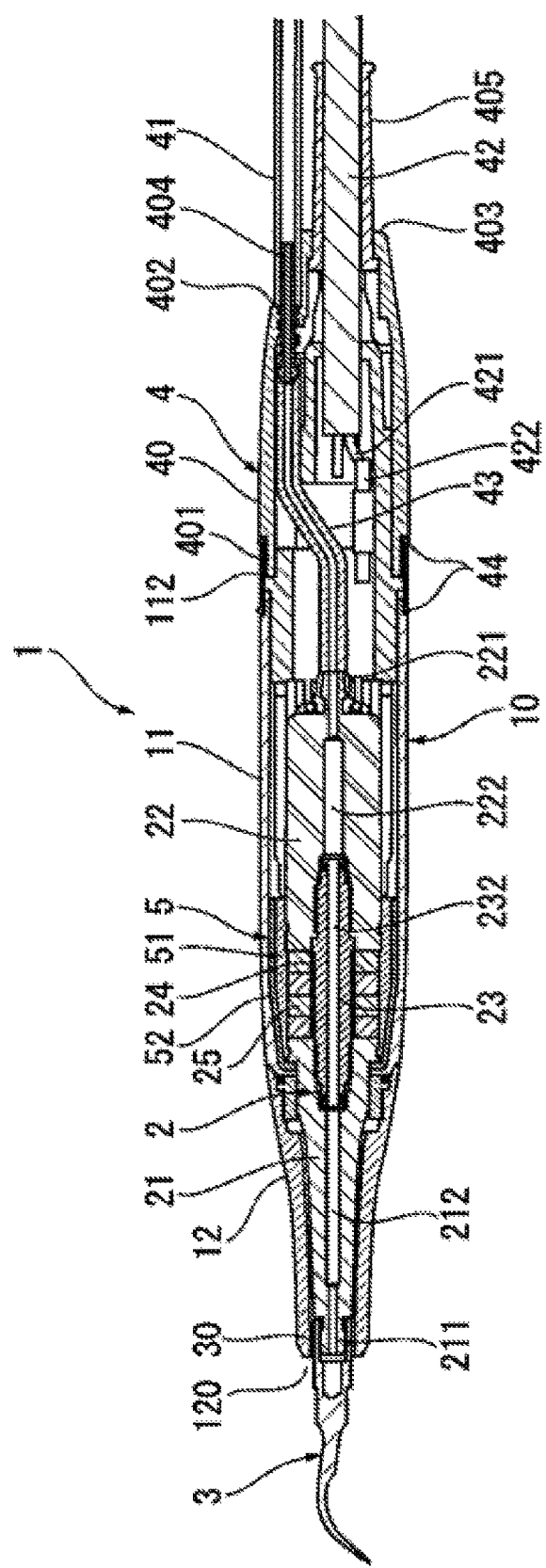
FIG. 1 is a longitudinal sectional view of an embodiment of an ultrasonic handpiece having a transducer cover according to the present invention.

FIG. 1 illustrates an ultrasonic dental handpiece equipped with a transducer cover according to the present invention. Ultrasonic handpiece 1 has body casing 10. To the distal end of the body casing 10 is detachably attached dental tool tip 3, while to the proximal end is detachably attached connector 4 for providing connection to a power source and a cooling water source. Ultrasonic generator 2 is contained in the body casing 10, and provided with power and cooling water via the connector 4.

Figure 2:
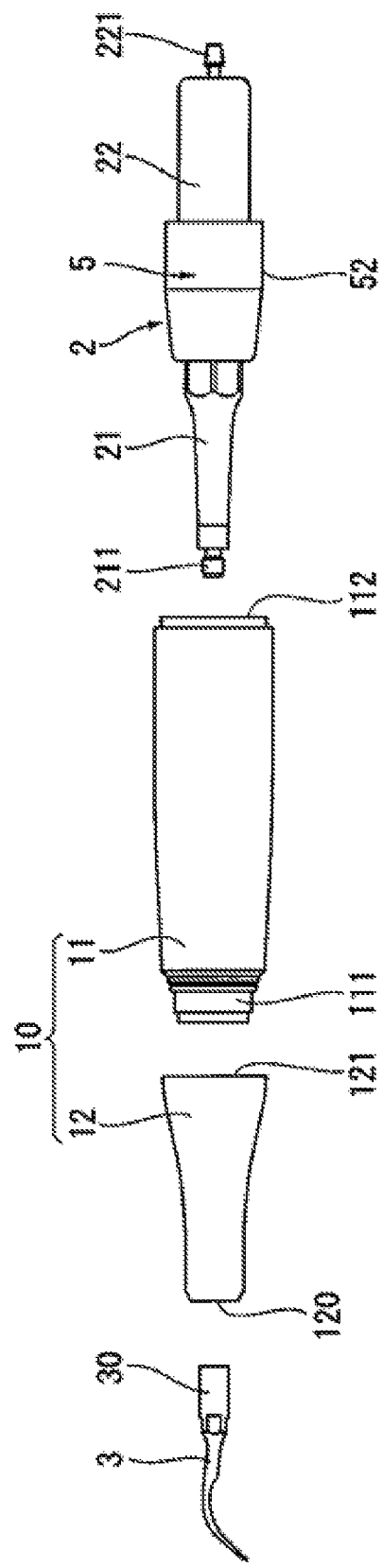
FIG. 2 is an exploded side view showing the body casing, ultrasonic generator, and tip of the ultrasonic handpiece of FIG. 1.

The body casing 10 is composed of case 11 and cap 12 connected to the distal end of the case 11, as shown in FIG. 2. The case 11 is generally in the form of a slightly distally tapered hollow cylinder, and has an annular projection of a reduced diameter on its distal end and a threaded inner surface 112 at its proximal end. The circumferential surface of the annular projection is formed with thread 111. The cap 12 is generally in the form of a distally tapered hollow cylinder, and has small opening 120 at its distal end for receiving the tip 3 therein and large opening at its proximal end for receiving the distal end portion of the case 11. Thread 121 is formed in the inner surface of the cap 12 in its proximal end portion so as to mesh with the thread 111 on the case 11. In this way, the case 11 and the cap 12 are detachably connected via the threads 111 and 121.

Figure 3:
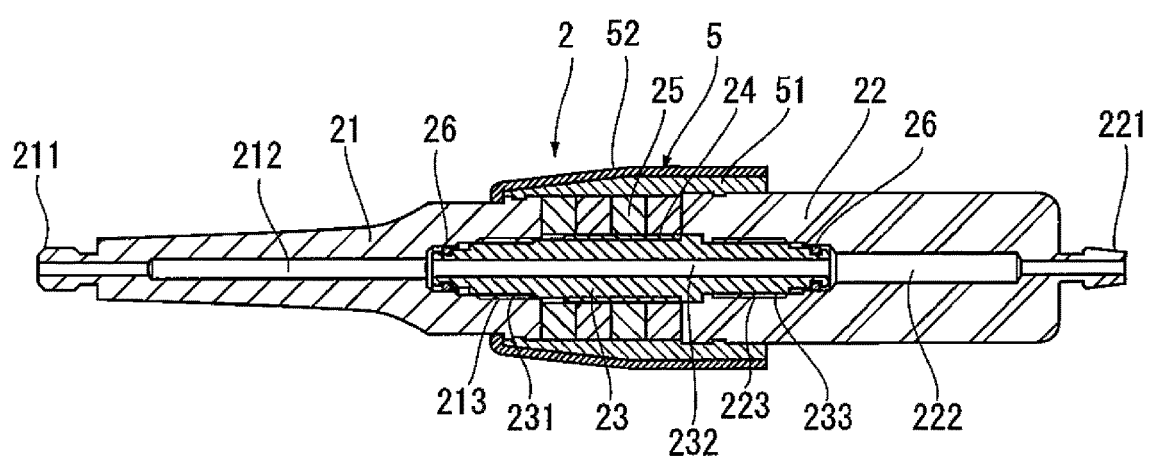
FIG. 3 is an enlarged longitudinal sectional view of the ultrasonic generator and the transducer cover of the ultrasonic handpiece of FIG. 1.

As shown in FIGS. 2 and 3, the ultrasonic generator 2 has front horn 21, rear horn 22, connecting member 23 connecting these two horns 21 and 22, and transducer 25 held between the front and rear horns 21 and 22 and arranged around the connecting member 23 via insulator tube 24.

The front horn 21 has a distally tapered contour so as to fit in the cap 12, and has plug 211 at its distal end, on which the tip 3 is to be fitted. Water channel 212 is formed through the front horn 21 along the axial center thereof with an enlarged proximal portion, which is formed with thread 213. The rear horn 22 has a generally cylindrical contour so as to fit in the case 11, and has connector port 221 on its proximal end. Water channel 222 is formed through the rear horn 22 along the axial center thereof with an enlarged distal portion, which is formed with thread 223. The connector port 221 forms a proximal extension of the water channel 222.

The connecting member 23 is a connecting rod generally in the form of a cylinder having a diameter smaller than those of the front and rear horns 21 and 22. Water channel 232 is formed through the connecting member 23 along the axial center thereof for providing fluid communication between the water channels 212 and 222 of the front and rear horns 21 and 22. The connecting member 23 has a distal portion which is threaded 231 on the outer surface so as to mesh with the thread 213 in the proximal end portion of the front horn 21, a proximal portion which is threaded 233 on the outer surface so as to mesh with the thread 223 in the distal end portion of the rear horn 22, and a middle portion forming a surface on which the transducer 25 is attached. The insulator tube 24 fits on the middle portion. The transducer 25 is in an annular form, and is arranged around and attached to the middle portion of the connecting member 23 with the insulator tube 24 interposed between the transducer 25 and the connecting member 23. Lead wires extend from electrodes of the transducer 25.

O-ring 26 is fitted on each end of the connecting member 23, and the connecting member 23 is screwed together with the front horn 21 with the distal thread 231 meshing with the proximal thread 213, and with the rear horn 22 with the proximal thread 233 meshing with the distal thread 223. In this way, the front horn 21 and the rear horn 22 are connected via the connecting member 23, and the transducer 25 fitted around the connecting member 23 on its middle portion via the insulator tube 24 is arranged and held between the front and rear horns 21 and 22.

Transducer cover 5 is provided over and around the transducer 25 so as to fix the ultrasonic generator 2 in the body casing 10 and to block or at least reduce transmission of vibration of the transducer 25 to the body casing 10. The ultrasonic generator 2 provided with the transducer cover 5 is then placed in the body casing 10. At the ends of the lead wire s extending from the transducer 25, terminals are connected, which are arranged in the proximal opening of the case 11.

Tip 3 is available in various forms as is well known in the art, so that detailed discussion about its form is eliminated. In any case, the proximal portion of the tip 3 forms attachment end 30, which is formed generally in a cylindrical form sized and shaped to be inserted into the distal opening 120 of the cap 12 and fitted onto distal plug 211 of the front horn 21. The tip 3 is inserted into the distal end of the body casing 10 and operatively connected to the ultrasonic generator 2.

Referring back to FIG. 1, connector 4 has connector case 40, which has a proximally tapered, generally cylindrical form, and has an annular projection at the distal end, which has a smaller diameter and is formed with thread 401 on its outer surface. In the proximal end of the connector case 40 is formed opening 402, in which connector pipe 404 is inserted, and opening 403, in which connector pipe 405 is inserted. One end of the connector pipe 404 outside the connector case 40 is connected to the cooling water tube 41 extending from the water source, and the other end inside the connector case 40 is connected to cooling water tube 43 to be connected to the ultrasonic generator 2. The connector pipe 405 receives therein power supply cable 42 extending from the power source. Wiring 421 bundled in the power supply cable 42 is connected to terminals 422, which are arranged in the distal opening of the connector case 40.

Next, the transducer cover 5 used in the handpiece 1 is explained in detail. Referring to FIGS. 2 and 3, the transducer cover 5 has at least two coaxial layers, namely, vibration absorbing layer 51 made of a synthetic resin having a vibration absorbing property, and chemical blocking layer 52 made of a synthetic resin which is impermeable to water and chemicals. These two layers have a first axial through-channel 51A and a second axial trough-channel 51B, respectively, and are sealing laminated over and around the transducer 25.

The vibration absorbing layer 51 is made of rubber, such as silicon rubber, having a vibration absorbing property. The chemical blocking layer 52 is made of rubber, such as silicon rubber, having resistance to water, heat, and chemicals, and rendered impermeable by compression molding. The chemical blocking layer 52 extends beyond the vibration absorbing layer 51 at least distally to cover the distal end of the vibration absorbing layer 51 and be sealingly attached to the front horn 21. In this way, the layers 51 and 52 are sealingly laminated around the transducer 25, with the vibration absorbing layer 51 being the inner layer and the chemical blocking layer 52 being the outer layer.

Figure 4:
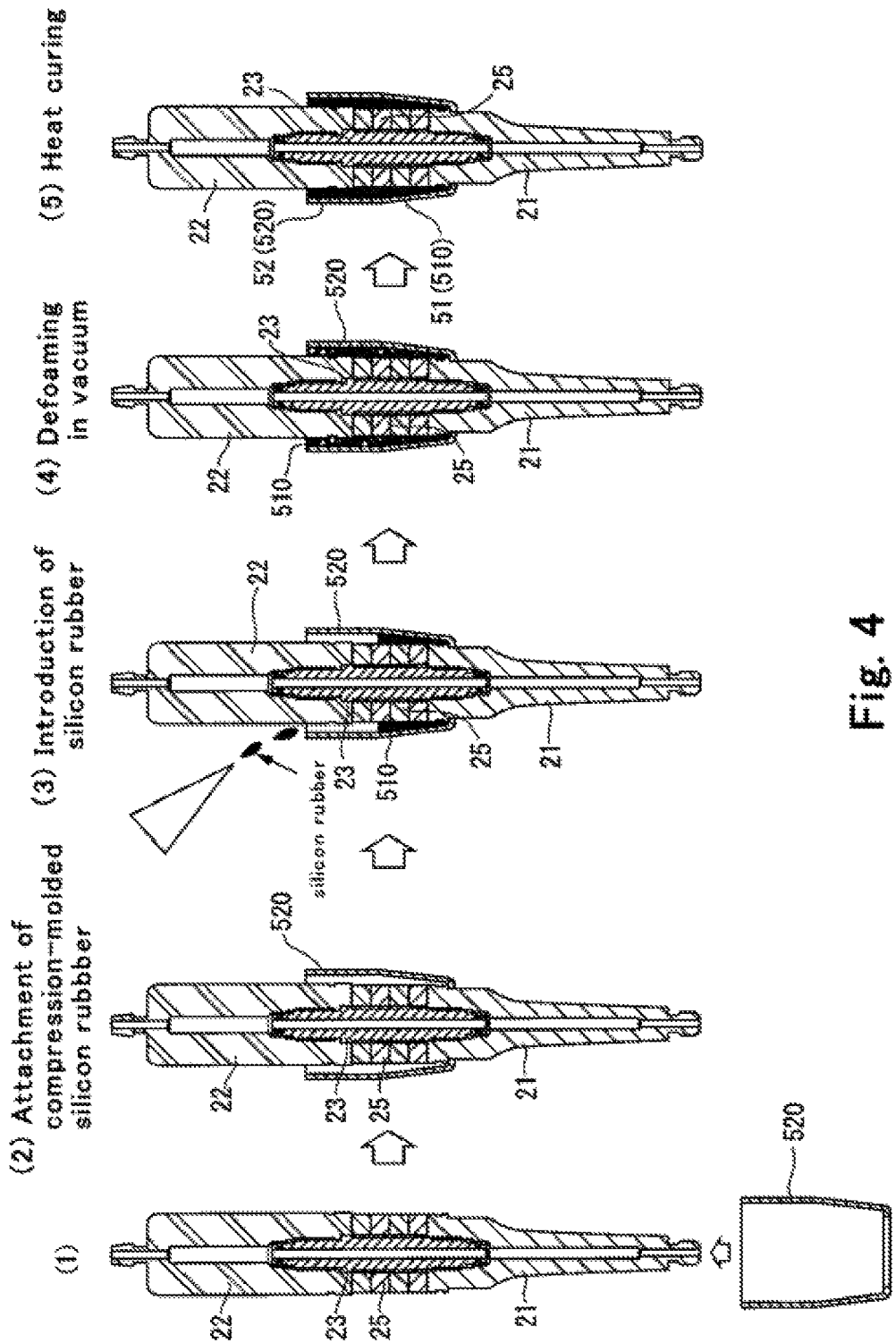
FIG. 4 illustrates how the transducer cover of the ultrasonic handpiece of FIG. 1 is formed.

FIG. 4 illustrates how this transducer cover 5 is formed. First, as shown in FIGS. 4(1) and 4(2), cylindrical member 520 made of a synthetic resin which is impermeable to water and chemicals, is arranged around the transducer 25 (Step 1). In this embodiment, the cylindrical member 520 is made of compression silicon rubber. The cylindrical member 520 has an enough length to enclose the entire transducer 25, with the distal end reaching the circumferential surface of the front horn 21 and the proximal end reaching the circumferential surface of the rear horn 22. The cylindrical member 520 is distally tapered so that the distal end is sealingly attached to the front horn 21.

Next, as shown in FIG. 4 (3), an elastic, thermosetting synthetic resin, in this case silicon rubber 510 in liquid form, is poured inside the cylindrical member 520 to form a layer between the transducer 25 and the cylindrical member 520 in contact therewith (Step 2). Then, the silicon rubber 510 in liquid form is vacuum defoamed as shown in FIG. 4 (4) (Step 3), and thermally cured as shown in FIG. 4(5) (Step 4).

Through these Steps 1 to 4, the transducer cover 5 is formed over and around the transducer 25 by sealingly laminating the vibration absorbing layer 51 and the chemical blocking layer 52. Here, the chemical blocking layer 52 extends distally beyond and covers the distal end of the vibration absorbing layer 51 and is sealingly fixed on the circumferential surface of the front horn 21, and extends proximally together with the vibration absorbing layer 51 to the circumferential surface of the rear horn 22.

The ultrasonic generator 2, on which the transducer cover 5 is thus formed around the transducer 25, is then placed in the body casing 10 as shown in FIG. 1. The transducer cover 5 is compressed between the inner surface of the case 11 and the outer surface of the transducer 25, and by means of the elastic restoration of the transducer cover 5, the ultrasonic generator 2 is snugly fixed in the body casing 10.

Then the connector 4 is connected to the proximal end of the body casing 10 via O-ring 44, by which the cooling water tube 43 in the connector 4 is connected to the connector port 221 forming an extension of the water channel 222 in the ultrasonic generator 2, and the wiring 421 in the connector 4 is connected via the terminals to the lead wires extending from the transducer 25. The proximal thread 112 on the inner surface of the body casing 10 meshes with the distal thread 401 on the outer surface of the connector 4 to connect the body casing 10 and the connector 4.

Figure 5:
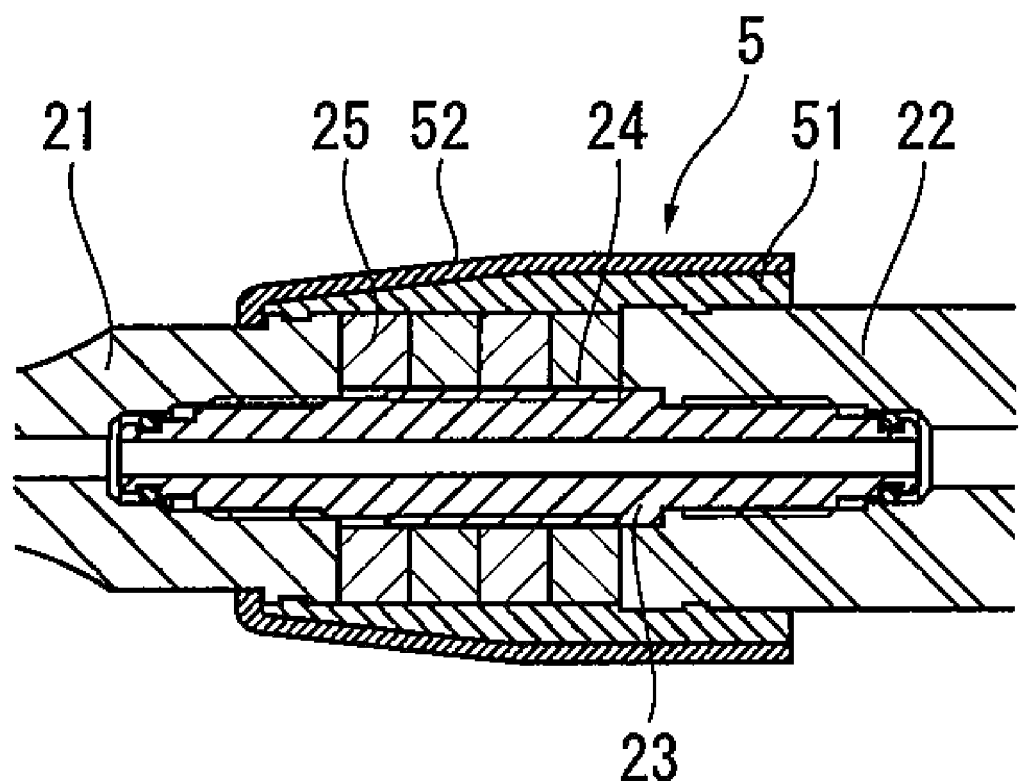
FIG. 5 is an enlarged longitudinal sectional view of the transducer cover of the ultrasonic handpiece of FIG. 1, showing its two-layered structure.

In the ultrasonic handpiece 1, as shown in FIG. 5, the transducer cover 5 has the vibration absorbing layer 51 and the chemical blocking layer 52, which are sealingly laminated around the transducer 25, with the vibration absorbing layer 51 sealingly attached to the transducer 25 and the chemical blocking layer 52 sealingly attached to the vibration absorbing layer 51. The vibration absorbing layer 51 absorbs vibration of the transducer 25 to block or at least reduce transmission of the vibration to the body casing 10. The chemical blocking layer 52 blocks permeation of liquid, such as chemicals. Thus even when the ultrasonic handpiece 1 is subjected to washing with hot water containing alkaline or acidic chemicals in addition to autoclaving or other sterilization treatment, permeation of chemical s maybe securely blocked due to the impermeability of the chemical blocking layer 52. The transducer cover 5 is also effective in immersion cleaning in alkaline or acidic chemicals. While the conventional properties such as vibration absorption and resistance to water, heat, and chemicals are maintained, the transducer cover 5 is rendered impermeable to water and chemicals. Thus insulation failure of the transducer 25 caused by permeation and adhesion of chemicals to the electrodes of the transducer 25 may securely be prevented.

Further, since the vibration absorbing layer 51 and the chemical blocking layer 52 are laminated with the former being the inner layer and the latter being the outer layer, even when the ultrasonic handpiece is subjected to cleaning with hot water containing alkaline or acidic chemicals, or immersion cleaning in alkaline or acidic chemicals, the chemicals are blocked by the outer chemical blocking layer 52 and will not reach the vibration absorbing layer 51. Since the chemical blocking layer 52 extends beyond the vibration absorbing layer 51 at least distally to cover the distal end of the vibration absorbing layer and be sealingly attached to the front horn 21, the chemicals will not enter through the distal end of the vibration absorbing layer 51.

Figure 6:
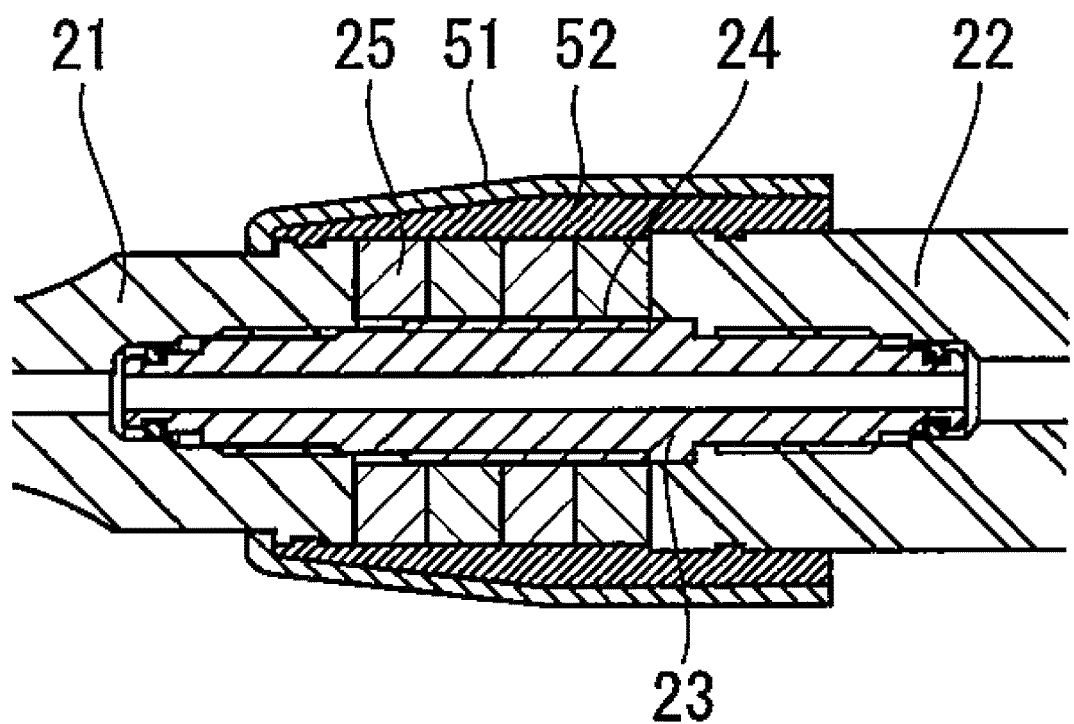
FIG. 6 is an enlarged longitudinal sectional view similar to FIG. 5, showing another embodiment of the transducer cover.
Figure 7:
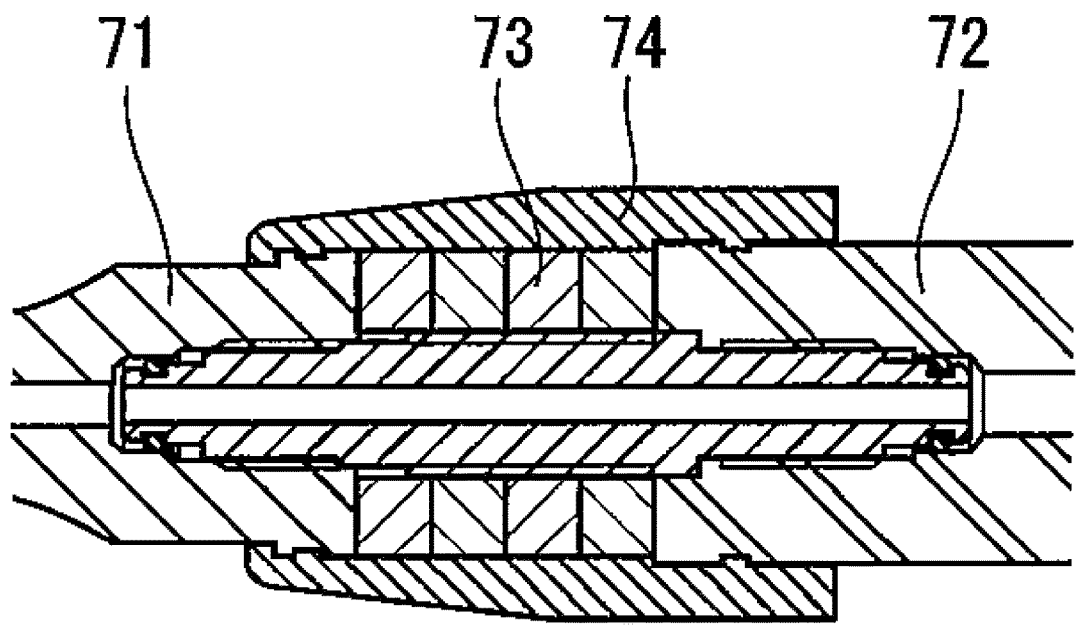
FIG. 7 is an enlarged longitudinal sectional view showing the structure of a conventional transducer cover.
Figure 8:
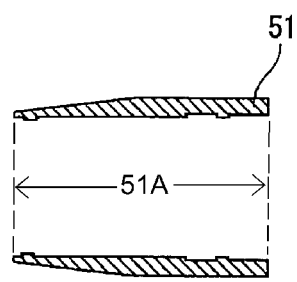
FIG. 8 is an enlarged longitudinal sectional view of the vibration absorbing layer of the embodiment of the transducer cover of FIG. 5.
Figure 9:
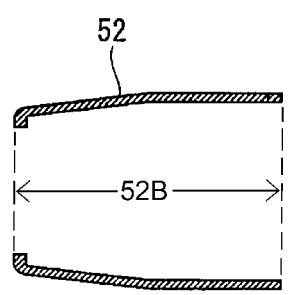
FIG. 9 is an enlarged longitudinal sectional view of the chemical blocking layer of the embodiment of the transducer cover of FIG. 5.

The method for forming the transducer cover 5 according to the present invention includes the steps of arranging the cylindrical member 520 made of a synthetic resin impermeable to water and chemicals around the transducer 25, arranging the elastic, thermosetting synthetic resin material in liquid form inside the cylindrical member 520 in contact therewith to form a layer, vacuum defoaming the synthetic resin in liquid form, and thermally curing the synthetic resin in liquid form. Through these steps, the transducer cover 5 having a vibration absorbing layer 51 which absorbs vibration of the transducer 25 to block or at least reduce transmission of the vibration to the body casing 10, and a chemical blocking layer 52 which blocks permeation of liquid containing chemicals, is formed sealingly laminated over and around the transducer 25. Thus, the transducer cover 5 having the vibration absorbing layer 51 and the chemical blocking layer 52 may be securely and easily provided over and around the transducer 25. By introducing the synthetic resin 510 in liquid form inside the cylindrical member 520, a mold or the like means for holding the resin 510 in liquid form may be eliminated, to facilitate formation of sealingly laminated vibration absorbing layer 51 and the chemical blocking layer 52. In the embodiment described above, the transducer cover 5 has two layers, namely, vibration absorbing layer 51 and the chemical blocking layer 52. However, the transducer cover 5 may have three or more layers including a plurality of the vibration absorbing layer 51 and/or the chemical blocking layer 52, or including an additional layer having resistance to water, heat, and chemicals, inside, outside, or between the vibration absorbing layer 51 and the chemical blocking layer 52. With such a structure, the above effects of the transducer cover 5 may further be improved. In the embodiment described above, the vibration absorbing layer 51 is laminated as the inner layer and the chemical blocking layer 52 is laminated as the outer layer around the transducer 25. However, as shown in FIG. 6, the chemical blocking layer 52 may be laminated as the inner layer and the vibration absorbing layer 51 may be laminated as the outer layer. Even with this structure, nearly the same effects as described above may be achieved.

For forming a transducer cover of this structure, the cylindrical member 520 is sized so as to sealingly contact over and around the transducer 25, and the elastic, thermosetting, synthetic resin 510 in liquid form may be introduced into a mold arranged around the cylindrical member 520, to form a layer of the resin 510 around the cylindrical member 520 in contact therewith.

The vibration absorbing layer 51 in the above embodiment is made of silicon rubber, but may alternatively be made of other rubber material or other synthetic resin as long as the material absorbs vibration of the transducer. Similarly, the chemical blocking layer 52 in the above embodiment is made of compression silicon rubber, but may alternatively be made of other compression rubber or other synthetic resin as long as the material is impermeable to water and chemicals. Even with such structure, the same effects as described above may be achieved. Further, the chemical blocking layer 52 may be produced by coating a synthetic resin layer having resistance to water, heat, and chemicals, with an impermeable material, or by overlaying and adhering an impermeable material layer to a synthetic resin layer having resistance to water, heat, and chemicals.

Further, the chemical blocking layer 52 may extend beyond the vibration absorbing layer 51 also proximally to cover the proximal end of the latter and be sealingly adhered to the rear horn 22. With such a structure, the above effects may further be improved.

What is claimed is:

1. A transducer cover for use in an ultrasonic medical instrument having a transducer, comprising:
    a vibration absorbing layer of a hollow-cylindrical form having a first axial through-channel, and made of a synthetic resin having a vibration absorbing property, and
    a chemical blocking layer of a hollow-cylindrical form having a second axial through-channel, and made of a synthetic resin which is impermeable to water and chemicals,
    wherein said vibration absorbing layer and said chemical blocking layer are coaxially laminated, and in a sealing arrangement over and around the transducer along a longitudinal axis of the transducer, and said transducer is arranged inside the first axial through-channel and inside the second axial through-channel,
    wherein said vibration absorbing layer is an inner layer and said chemical blocking layer is an outer layer, with said chemical blocking layer sealingly attached to said vibration absorbing layer,
    wherein said chemical blocking layer extends beyond said vibration absorbing layer at least distally to cover a distal end of the vibration absorbing layer, and
    wherein said chemical blocking layer extends beyond said vibration absorbing layer also proximally to cover a proximal end of the vibration absorbing layer.

2. The transducer cover according to claim 1, wherein said vibration absorbing layer is made of rubber having a vibration absorbing property.

3. The transducer cover according to claim 1, wherein said chemical blocking layer is made of rubber having resistance to water, heat, and chemicals, and rendered impermeable by compression molding.

4. The transducer cover according to claim 1, wherein said vibration absorbing layer does not extend beyond said chemical blocking layer either distally or proximally.

* * * * *